(12) United States Patent
Anderson et al.

(10) Patent No.: US 11,674,288 B2
(45) Date of Patent: Jun. 13, 2023

(54) SYSTEM AND METHOD FOR OBSCURANT MITIGATION

(71) Applicant: Deere & Company, Moline, IL (US)

(72) Inventors: Noel W. Anderson, Fargo, ND (US); Zachary T. Bonefas, Grimes, IA (US)

(73) Assignee: Deere & Company, Moline, IL (US)

(*) Notice: Subject to any disclaimer, the term of this patent is extended or adjusted under 35 U.S.C. 154(b) by 770 days.

(21) Appl. No.: 16/599,380

(22) Filed: Oct. 11, 2019

(65) Prior Publication Data
US 2020/0375083 A1   Dec. 3, 2020

Related U.S. Application Data

(60) Provisional application No. 62/854,922, filed on May 30, 2019.

(51) Int. Cl.
*A01B 69/04* (2006.01)
*G01N 15/02* (2006.01)
(Continued)

(52) U.S. Cl.
CPC ............ *E02F 9/205* (2013.01); *A01B 69/008* (2013.01); *A01D 41/1278* (2013.01);
(Continued)

(58) Field of Classification Search
CPC .............. A01B 69/008; A01D 41/1278; G01N 15/0227; G01N 15/06; G01N 33/0063;
(Continued)

(56) References Cited

U.S. PATENT DOCUMENTS

| 7,110,881 B2 | 9/2006 | Gray et al. |
| 7,167,797 B2 | 1/2007 | Faivre et al. |

(Continued)

OTHER PUBLICATIONS

Margaret Kovar et al, Dust emission research may lead to reduction of air pollutants, NM State News Center, Mar. 16, 2009, pp. 2. [online], [retrieved on Nov. 19, 2019]. Retrieved from the Internet: <URL: http://newscenter.nmsu.edu/Articles/view/4441>.

(Continued)

*Primary Examiner* — David Z Huang

(57) ABSTRACT

In accordance with an example embodiment, a system and method for obscurant mitigation is disclosed. The system comprises an obscurant assessor configured to characterize one or more characteristics of a detected obscurant and generate an obscurant model; an obscurant mitigator configured to perform one or more mitigation operations; and a controller communicatively coupled to each of the obscurant assessor and the obscurant mitigator. The controller is configured to receive an output signal from a vehicle sensor corresponding to a detected obscurant level and determine if the detected obscurant level exceeds a predetermined threshold. The controller generates an obscurant mitigation plan if the detected obscurant level exceeds the predetermined threshold based on the obscurant model generated by the obscurant assessor; and controls operations of an obscurant mitigator based on the obscurant mitigation plan to reduce the detected obscurant level.

22 Claims, 12 Drawing Sheets

(51) Int. Cl.

| | | |
|---|---|---|
| *E02F 9/20* | (2006.01) | |
| *G01W 1/02* | (2006.01) | |
| *E02F 9/26* | (2006.01) | |
| *G05D 1/02* | (2020.01) | |
| *G05D 1/00* | (2006.01) | |
| *G07C 5/00* | (2006.01) | |
| *A01D 41/127* | (2006.01) | |
| *G01N 15/06* | (2006.01) | |
| *G01N 33/00* | (2006.01) | |
| *G01N 15/00* | (2006.01) | |

(52) U.S. Cl.
CPC ............ *E02F 9/2054* (2013.01); *E02F 9/262* (2013.01); *G01N 15/0227* (2013.01); *G01N 15/06* (2013.01); *G01N 33/0063* (2013.01); *G01W 1/02* (2013.01); *G05D 1/0022* (2013.01); *G05D 1/0212* (2013.01); *G05D 1/0219* (2013.01); *G07C 5/008* (2013.01); *G01N 2015/0046* (2013.01); *G01N 2015/0693* (2013.01); *G01N 2033/0068* (2013.01); *G05D 2201/0207* (2013.01)

(58) Field of Classification Search
CPC ... G01N 2015/0046; G01N 2015/0693; G01N 2033/0068; G05D 1/0212
See application file for complete search history.

(56) References Cited

U.S. PATENT DOCUMENTS

| | | | |
|---|---|---|---|
| 7,313,478 B1 | 12/2007 | Anderson et al. | |
| 7,409,743 B2 | 8/2008 | Di Anna | |
| 7,415,333 B2 | 8/2008 | Anderson | |
| 8,056,313 B1 | 11/2011 | Flora et al. | |
| 8,191,346 B2 | 6/2012 | Flora et al. | |
| 8,347,595 B1 | 1/2013 | Flora et al. | |
| 9,043,129 B2 | 5/2015 | Bonefas et al. | |
| 9,795,913 B1* | 10/2017 | Flora | A01D 51/002 |
| 10,188,024 B2 | 1/2019 | Rusciolelli et al. | |
| 2006/0200334 A1 | 9/2006 | Faivre et al. | |
| 2011/0295423 A1 | 12/2011 | Anderson | |
| 2016/0217690 A1 | 7/2016 | Yamasaki et al. | |
| 2016/0298306 A1* | 10/2016 | de Kontz | G05D 1/0219 |
| 2017/0311534 A1 | 11/2017 | Rusciolelli et al. | |
| 2017/0314232 A1 | 11/2017 | Chi et al. | |
| 2019/0129435 A1* | 5/2019 | Madsen | B62D 6/001 |

OTHER PUBLICATIONS

Mark J. Rood et al, Remote Sensing of Dust Plume from Movement of Tracked Vehicles, pp. 2. [online], [retrieved on Nov. 19, 2019]. Retrieved from the Internet: <URL: http://aqes.cee.illinois.edu/research%20areas/lidar/trackedvehicles/trackedvehicles.htm>.

Miguel Alvarado et al, Towards the development of a low cost airborne sensing system to monitor dust particles after blasting at Open-Pit Mine Sites, Aug. 2015, pp. 27, <DOI: 10.3390/s150819667>, [online], [retrieved on Nov. 19, 2019]. Retrieved from the Internet: <URL: https://www.ncbi.nlm.nih.gov/pmc/articles/PMC4570391/>.

Jasper F Kok et al, The physics of wind-blown sand and dust, pp. 119, [online], [retrieved on Nov. 19, 2019]. Retrieved from the Internet: <URL: https://arxiv.org/ftp/arxiv/papers/1201/1201.4353.pdf>.

Thomas H Meyer et al, A Dynamic Lagrangian, Field-scale Model of Dust Dispersion from Agricultural Tilling Operations, Department of Natural Resources and the Environment Articles, Jan. 1, 2008, pp. 13, [online], [retrieved on Nov. 19, 2019]. Retrieved from the Internet: <URL: http://opencommons.uconn.edu/cgi/viewcontent.cgi?article=1009&context=nrme_articles>.

Grain Handling Operations and Dust Control Information, Sep. 2016, pp. 3, [online], [retrieved on Nov. 19, 2019]. Retrieved from the Internet: <URL: https://www.illinois.gov/dceo/SmallBizAssistance/EnvironmentalAssistanceProgram/Documents/grain%20handling%20operations%20dust%20control.pdf>.

David Eddy, Videos Focus on Minimizing Almond Harvest Dust, Jul. 31, 2016, pp. 6, [online], [retrieved on Nov. 19, 2019]. Retrieved from the Internet: <URL: https://www.growingproduce.com/nuts/videos-focus-on-minimizing-almond-harvest-dust/>.

Dust Control, Santa Barbara Air Pollution Control District, pp. 5, [online], [retrieved on Nov. 19, 2019]. Retrieved from the Internet: <https://www.ourair.org/dust-control/>.

Large Scale Industrial Odour & Dust Suppression, MistCannon, pp. 6. [online], [retrieved on Nov. 19, 2019]. Retrieved from the Internet: <URL: https://www.environmental-expert.com/products/mistcannon-outdoor-dust-suppression-equipment-440299>.

Wind Blown Dust Monitoring and Modeling at Owens Lake, CA Duane, Great Basin Unified Air Pollution Control District, Jul. 2004, pp. 7. [online], [retrieved on Nov. 19, 2019]. Retrieved from the Internet: <URL: https://slideplayer.com/slide/6388678/>.

Barnes et al, Managing Dust on Unpaved Roads and Airports, Alaska Department of Transportation & Public Facilities, Oct. 2014, pp. 172, [online], [retrieved on Nov. 19, 2019]. Retrieved from the Internet: <URL: https://www.researchgate.net/publication/267866793_Managing_Dust_on_Unpaved_Roads_and_Airports_sg=TSMI6swtvie8iNP6Mm3YLLmuJ2TP9EEfO3nyQT5KM3I_1VdkQWKJ0eyif5Lh8iXf1hjHrle_sA>.

* cited by examiner

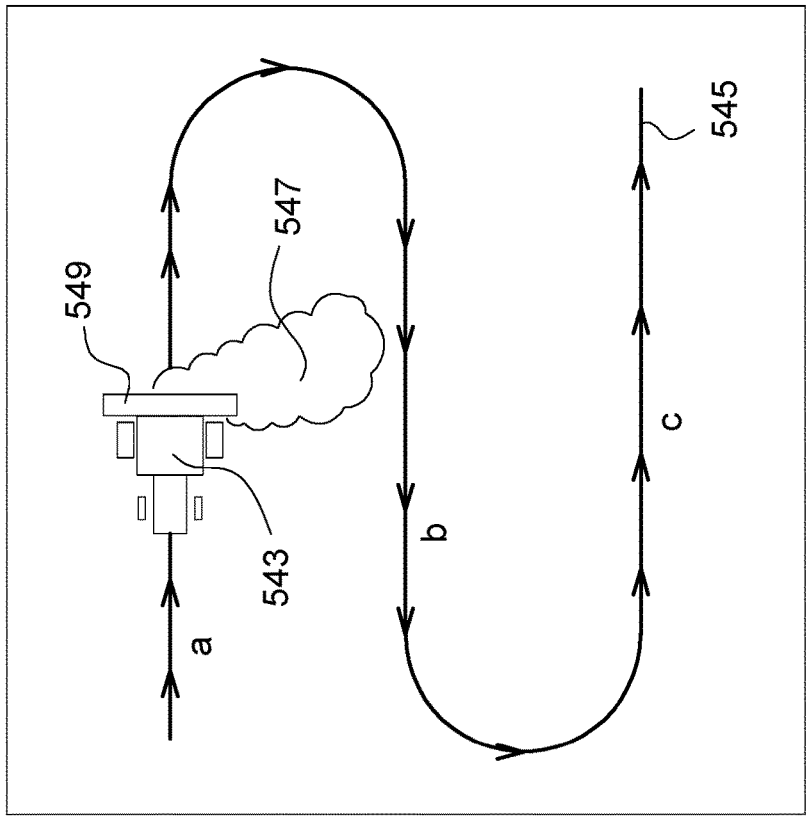
FIG. 5A
FIG. 5B

SYSTEM AND METHOD FOR OBSCURANT MITIGATION

RELATED APPLICATION

The Application claims priority to U.S. Application No. 62/854,922, titled "A System and Method for Obscurant Mitigation," filed May 30, 2019, and relates to U.S. application Ser. No. 12/898,157, titled "System and Method for Governing a Speed of an Autonomous Vehicle," filed Oct. 5, 2010, both of which are hereby incorporated by reference in their entirety.

FIELD OF THE DISCLOSURE

The present disclosure relates generally to detection systems and mitigation methods, and, more particularly, to a system and method for detecting and mitigating obscurants for a vehicle.

BACKGROUND OF THE DISCLOSURE

In off-road and on-road work machine applications, the use of perception or vision systems to improve work machine operations is well known. The effectiveness of such systems, however, can be substantially obstructed or reduced in harsh environmental conditions that include atmospheric obscurants.

To address such concerns, some conventional approaches employ the use of manual mitigation systems. With such systems, work machine components such as sweeper heads are manually adjusted and controlled by human operators to reduce dust accumulation. For example, the on/off operations, parameter inputs, or physical orientations of the components are adjusted by hand or via an operator interface. Drawbacks to such systems include decreased sensing perception, increased measurement errors, and increased costs. As such, automation is needed for systems where human operators may not be able to accurately monitor conditions relative to needs or for unmanned work machine operations.

Other conventional approaches employ the use particle and air cleaning devices to reduce air pollution generated by harvesting operations. For example, some systems utilize air stream cleaning techniques that operate to remove larger particles of foreign material from the air stream before these particles are passed through a fan, pulverized, and discharged into the atmosphere. A drawback, however, is that systems which include dedicated mitigation components often require mechanical, hydraulic, electrical or other power to operate, thereby leading to increased fuel consumption.

For example, with work machines that typically run at or near full power for their tasks, using work machine power for unnecessary mitigation may require primary functions to be operated at reduced speed. Other examples include limited power storage (e.g., battery) where unnecessary power usage can limit available running time or require a primary power source to be operated above a desired rating for a limited period.

To overcome drawbacks associated with the above approaches, other systems implement work machine speed control systems. With such systems, speed of a mobile work machine is adjusted based on an optical density of obscurant within the operating environment. Work machine speed control systems, however, have limited mitigation capabilities. Therefore, there is a need in the art for a robust and intelligent system that utilizes predictive and automated mitigation systems to optimize work machine performance.

SUMMARY OF THE DISCLOSURE

A system and method for obscurant mitigation that predicts an obscurant plume and mitigating its impact at the source by controlling a vehicle system to mitigate the size or optical density of the plume in a work machine's critical field of view is disclosed.

According to an aspect of the present disclosure, the system comprises an obscurant assessor configured to characterize one or more characteristics of a detected obscurant and generate an obscurant model; an obscurant mitigator configured to perform one or more mitigation operations; and a controller communicatively coupled to each of the obscurant assessor and the obscurant mitigator. The controller is configured to receive an output signal from a vehicle sensor corresponding to a detected obscurant level and determine if the detected obscurant level exceeds a predetermined threshold; generate an obscurant mitigation plan if the detected obscurant level exceeds the predetermined threshold based on the obscurant model generated by the obscurant assessor; and control operations of an obscurant mitigator based on the obscurant mitigation plan to reduce the detected obscurant level.

According to another aspect of the present disclosure, the system comprises an obscurant assessor arranged on at least one first work vehicle, wherein the obscurant assessor is configured to characterize one or more attributes of a detected obscurant and generate an obscurant model; an obscurant mitigator, wherein the obscurant mitigator is configured to perform one or more mitigation operations; and a controller communicatively coupled to each of the obscurant assessor and the obscurant mitigator. The controller is configured to receive an output signal from a vehicle sensor corresponding to a detected obscurant level and determine if the detected obscurant level exceeds a predetermined threshold associated with at least one second work vehicle; generate an obscurant mitigation plan if the detected obscurant level exceeds the predetermined threshold based on the obscurant model generated by the obscurant assessor; and control operations of the obscurant mitigator to control each of the first vehicle and the second vehicle based on the obscurant mitigation plan to reduce the detected obscurant level.

According to another aspect of the present disclosure, a method for obscurant mitigation is disclosed. The method comprises detecting a level of obscurant with an obscurant assessor; comparing, with a controller, the detected level of obscurant with a threshold value to determine if the detected level exceeds the threshold value; generating, with the controller, an obscurant mitigation plan if the detected level exceeds the threshold value; and controlling at least one obscurant mitigator based on the generated obscurant mitigation plan.

Other features and aspects will become apparent by consideration of the detailed description and accompanying drawings.

BRIEF DESCRIPTION OF THE DRAWINGS

The detailed description of the drawings refers to the accompanying figures in which:

FIG. 5A is an illustration of a work machine arrangement employing the first method according to an embodiment;

FIG. 5B is an illustration of a work machine arrangement employing the first method according to an embodiment;

Like reference numerals are used to indicate like elements throughout the several figures.

DETAILED DESCRIPTION OF THE DRAWINGS

Figure 1:
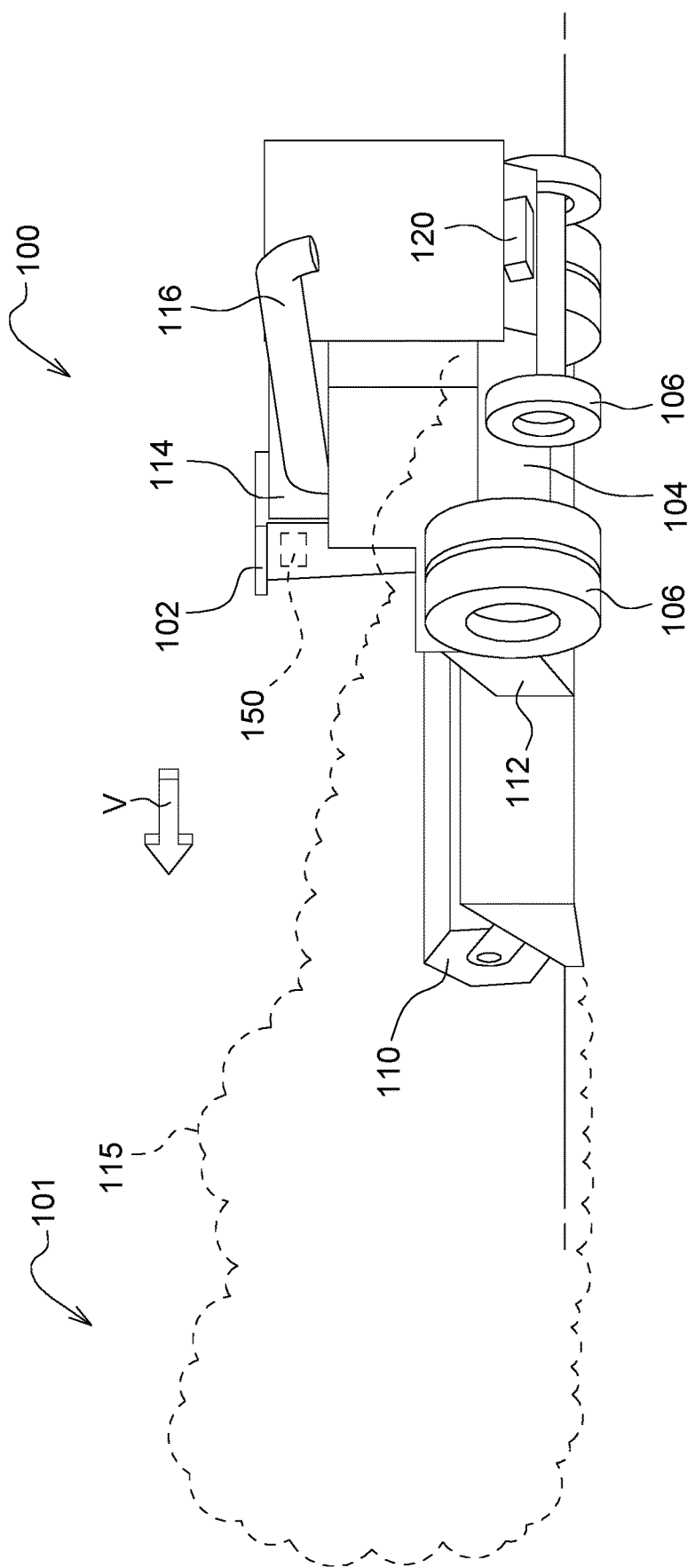
FIG. 1 is a left-side view of a work machine according to an embodiment.
Figure 2A:
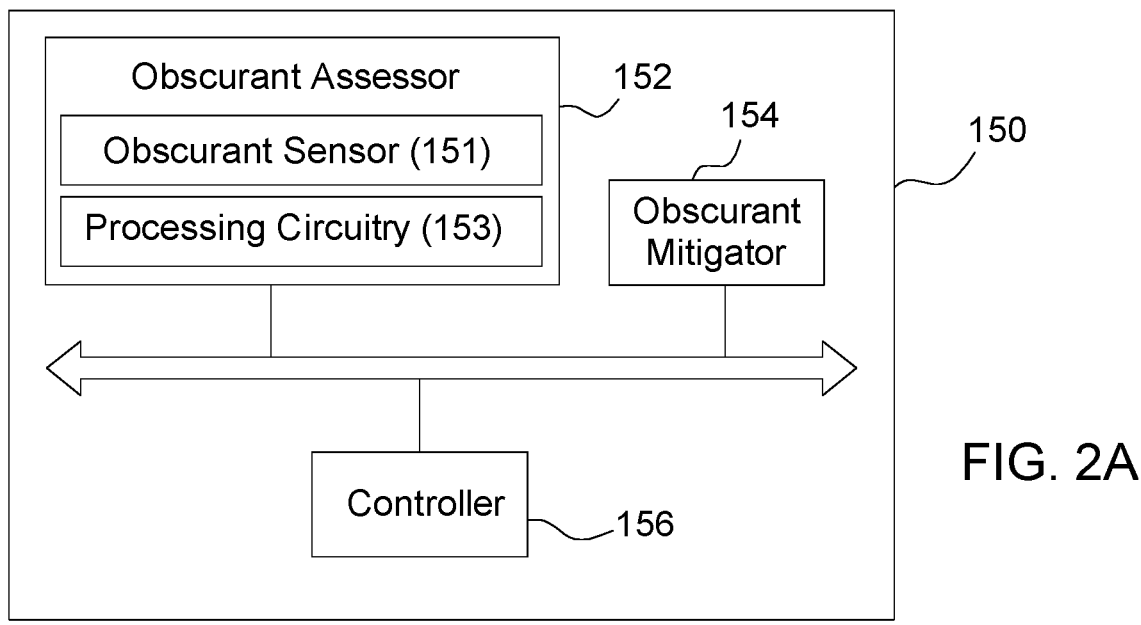
FIG. 2A is a block diagram of an obscurant mitigation system according to an embodiment.
Figure 2B:
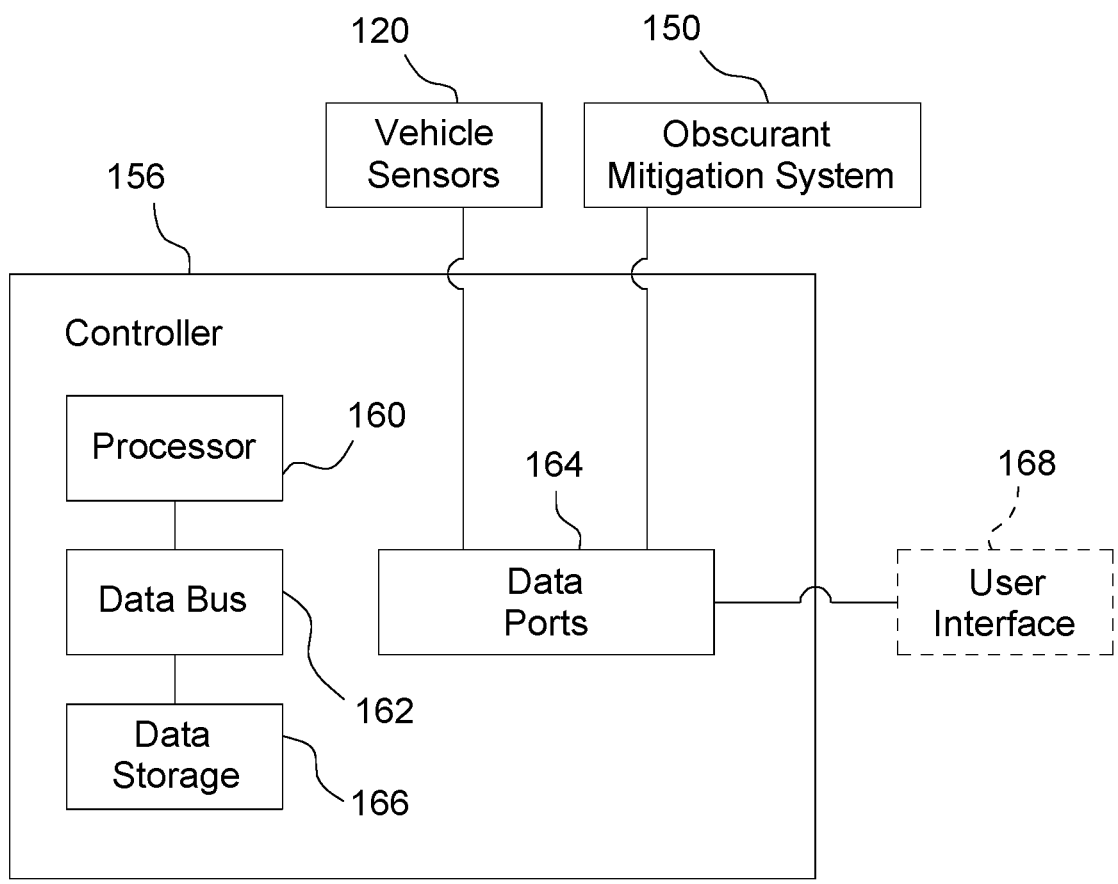
FIG. 2B is a block diagram of a control system according to an embodiment.

Referring to FIGS. 1 and 2, a work machine comprising an obscurant mitigation system 150 is shown according to an embodiment. Although in embodiments discussed herein, the obscurant mitigation system 150 is shown as being used in harvesting applications, it should be noted that the obscurant mitigation system 150 may be useful in a wide variety of applications. For example, in other embodiments, the obscurant mitigation system 150 may also be employed in tillage, earth moving and excavating, planting, seeding, sprayer, tree felling, mowing, snow plowing applications, or others, with embodiments discussed herein being merely for exemplary purposes to aid in an understanding of the present disclosure.

In some embodiments, the work machine can include an agricultural harvester 100 comprising a chassis 104 supported by a wheel assembly 106 (i.e., front wheels and rear wheels). An operator cab 102 can be provided at the front of the agricultural harvester 100, and can comprise an operator interface (not shown) or other suitable input devices which can be manipulated by the operator to change various machine settings.

A header 110 can be coupled to the agricultural harvester 100 via a feeder house 112 and is arranged to extend forward from the agricultural harvester 100. The agricultural harvester 100 drives in a forward direction, as indicated by the arrow V, over a worksite 101 and receives crop material from the header 110 for transfer into the feeder house 112. The feeder house 112 transfers the crop material in a grain tank 114 where it then conveyed into a grain cart (refer, e.g., to FIG. 3B) or truck from a spout 116. As the agricultural harvester 100 travels over the worksite 101 in the harvesting environment, the header 110 interaction with the crop material generates an accumulation of obscurant (i.e., an obscurant plume 115) that is detected and mitigated by the obscurant mitigation system 150. In FIG. 1, the obscurant plume 115 is shown as comprising dust. In other embodiments, the obscurant plume 115 can include, without limitation, smoke, fog, fire, snow, saw dust, vegetation parts, or others that may be generated by tire interaction with soil, chaff discharge, wind drafts across dry and bare soil, for example. In some examples, the presence of obscurant is widespread and forecastable from environmental information such as humidity, temperature, wind, and precipitation intensity. In other examples, there may not be an obscurant on a worksite until a work machine moves on the worksite or engages material on the worksite, often creating a more localized plume of obscurant which can also be forecast. Obscurant availability comprises conditions naturally creating obscurants (e.g., fog) as well as those that will create obscurants as work machine is active in the environment (e.g., dust kicked into the wind by tires of a moving machine).

One or more vehicle sensors 120 can be mounted to the agricultural harvester 100 in a variety of locations around the machine to capture images in a narrow or wide field of view, with FIG. 1 being one exemplary embodiment. The vehicle sensors 120 can comprise a variety of sensing devices, such as, e.g., cameras, stereo cameras, or lidar sensors, which can be used to monitor the environment around the agricultural harvester 100. Although example sensing devices are discussed herein, it should be noted that the vehicle sensors 120 can comprise any other suitable sensors capable of detecting obscurants. The vehicle sensors 120 may also be used for obstacle intelligence, feed-forward machine control, and/or for sensing the job quality of worksite 101.

In some embodiments, the obscurant mitigation system 150 can comprise an obscurant assessor 152 and an obscurant mitigator 154, each communicatively coupled to a controller 156 (FIG. 2). The obscurant assessor 152 can comprise at least one obscurant sensor 151 and internal processing circuitry 153. The obscurant sensor 151 can include, without limitation, laser sensors, density sensors, thermal imaging sensors, or other suitable sensors that are configured to measure obscurant attributes (e.g., optical density of the obscurant, signal attenuation, particle size distribution, or visibility distance). In other embodiments, rather than including dedicated obscurant sensors such as sensor 151, the obscurant mitigation system 150 can be configured to interface existing mitigation and sensing processing capabilities with perception sensors arranged on the work machine (e.g., obstacle intelligence sensors).

In some embodiments, the obscurant sensors 151 can be mounted on the agricultural harvester 100 (FIG. 1) in a forward facing, rearward facing, and/or a lateral facing direction. In other embodiments, the obscurant sensors 151 can be remotely mounted, e.g., on another work machine, on a manned or unmanned aerial work machine, on a stationary pole, or any other suitable platform. The internal processing circuitry 153 can comprise any suitable data processing device coupled to a database which stores obscurant models such as obscurant source models, internal machine data, obscurant plume models, environmental data, or others. For example, the obscurant models are accessible by the internal processing circuitry 153 and can be used collectively with machine data or sensor data received from the obscurant sensors 151 to model obscurant characteristics.

In some embodiments, attributes such as soil type, soil moisture, and wind velocity measured by the obscurant sensors 151 can be used to estimate where soil may become windborne, in what quantity, and an associated obscurant plume (e.g., obscurant plume 115). In other embodiments, data such as internal material other than grain ("MOG") of the agricultural harvester 100, residue distribution system information, work machine-to-work machine material transfer information (e.g., grain transfer from an agricultural harvester to a grain cart), and wind velocity can be used to model a harvest residue and obscurant plumes (e.g., obscurant plume 115). Additionally, data such as soil type, soil moisture, tire attributes, machine attributes, and wind velocity can be used to model obscurants generated by the wheels of the agricultural harvester 100.

The obscurant mitigator 154 can comprise a variety of obscurant removal or mitigation devices or systems such as, e.g., dust diverters, particulate cleaning systems, material application systems, path planning systems, that operate to perform mitigation tasks. The obscurant mitigator 154 operates to mitigate airborne obscurants or other obscurants in the agricultural harvester's critical field of view to increase visibility and/or performance of the vehicle sensors 120. As used herein, "critical field of view" refers to the portion of the total field of view that is essential for the obscurant mitigation system to perform successful mitigation operations. For example, in some embodiments, the critical field of view can be a region sensed by an obstacle intelligence system that allows the work machine (e.g., agricultural harvester 100) to dynamically respond to an issue or hazard to prevent damage. In other embodiments, the critical field of view can be a region that is sensed with data being used by a payload or task control system of the agricultural harvester 100 within a certain percentage of a measured value.

The controller 156 may send command data to the obscurant mitigator 154 to initiate the activation of one or more mitigation operations. In some embodiments, the controller 156 can be arranged locally as part of a work machine electronics unit of the agricultural harvester 100 or remotely at a remote processing center (not shown). The controller 156 can comprise an electronic data processor 160, data ports 164, and a data storage device 166 that is coupled to or communicates via a databus 162. In some embodiments, a user interface 168 can be optionally coupled to the controller 156 and can be arranged locally in the agricultural harvester 100 or remotely in another work machine or offsite. The user interface 168 can employ visual, audio, speech, haptic, or other suitable communication methods to communicate with a work machine operator. For example, an operator can input various information, commands, or preferences into the user interface 168 via one of the communication methods.

The electronic data processor 160 can comprise a microprocessor, a microcontroller, a central processing unit, a programmable logic array, a programmable logic controller, an application specific integrated circuit, a digital signal processor other suitable programmable circuitry that is adapted to perform data processing and/or system control operations. The data storage device 166 can comprise electronic memory, non-volatile random-access memory (RAM), optical storage device, or other suitable storage devices. The data storage device 166 (hard disk, memory, or databases) may store one or more of the following software modules for execution by the electronic data processor 160. For example, each of the modules can comprise executable software instructions, data structures for processing by electronic data processor 160.

As will be appreciated by those skilled in the art, FIGS. 1 and 2 are provided merely for illustrative and exemplary purposes and are in no way intended to limit the present disclosure or its applications. In other embodiments, the arrangement and/or structural configuration of the agricultural harvester 100 or the obscurant mitigation system 150 can and will vary. For example, as will be discussed in further detail with reference to FIGS. 3A-3C and 7-9, in some embodiments, the obscurant mitigation system 150 can be arranged in a multi-work machine arrangement comprising two or more work machines. In other embodiments, additional sensing or mission planning techniques may be employed as will be discussed with reference to FIG. 10.

Figure 3A:
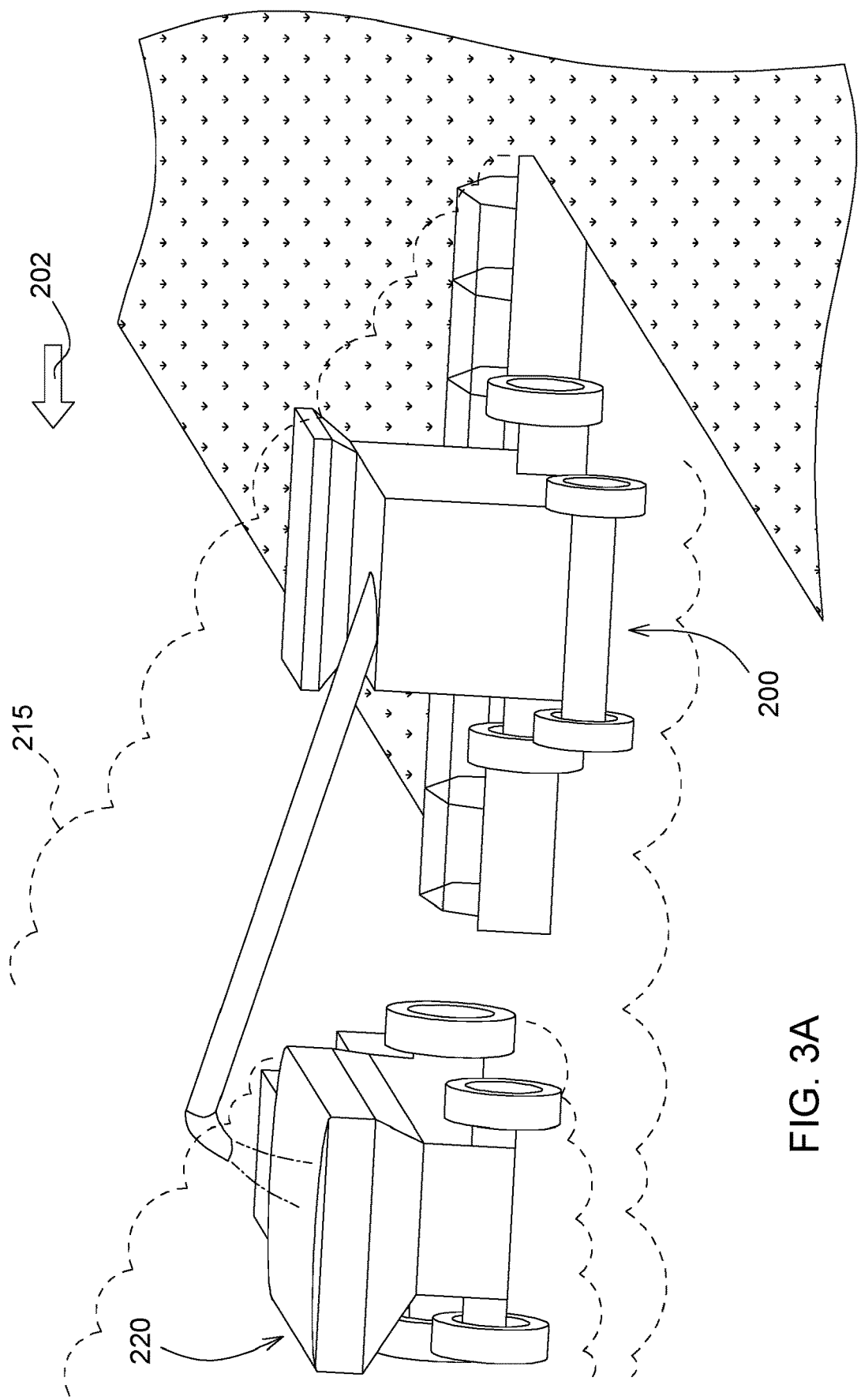
FIG. 3A is a front view of a work machine arrangement according to an embodiment.
Figure 3B:
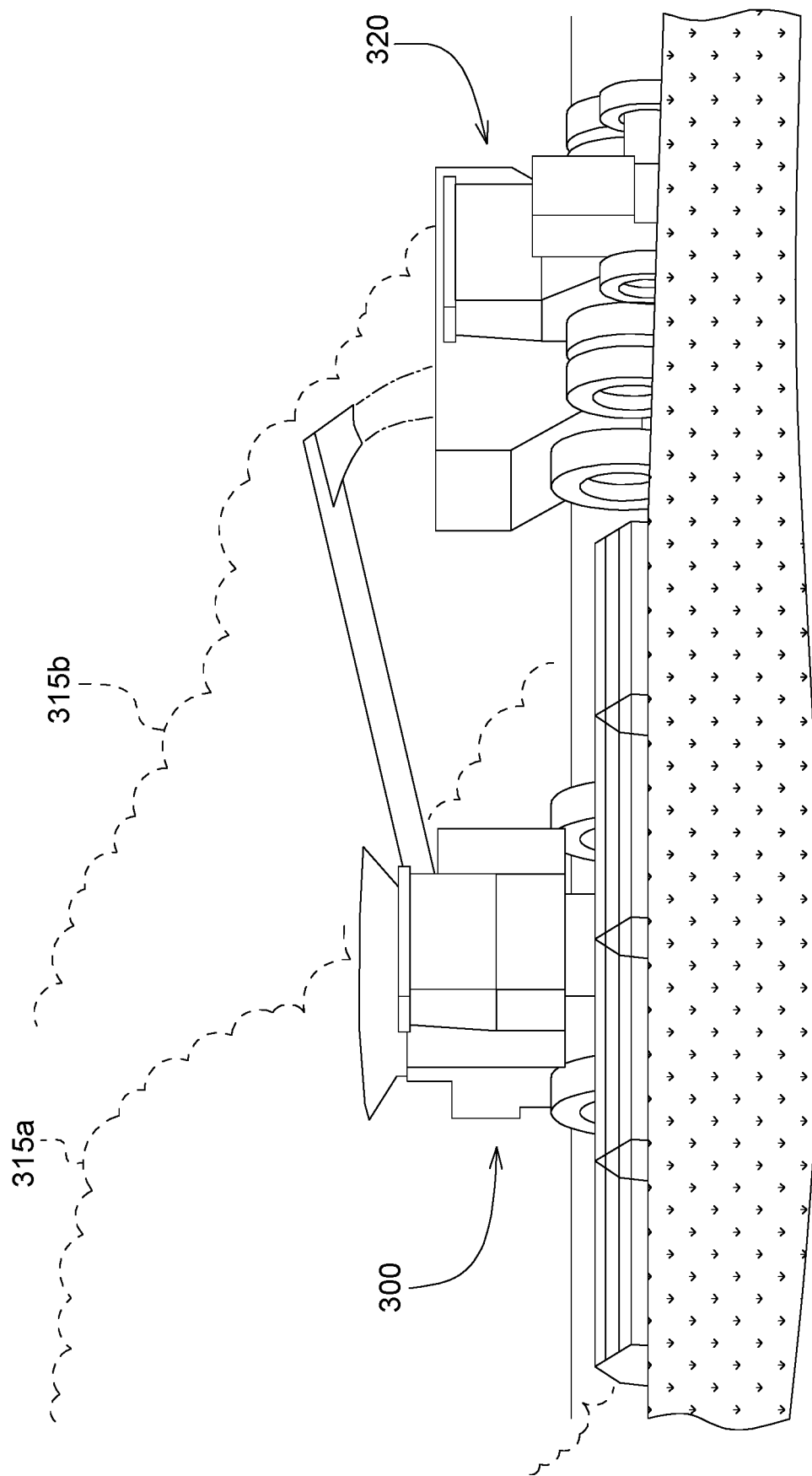
FIG. 3B is a front view of a work machine arrangement according to an embodiment.
Figure 3C:
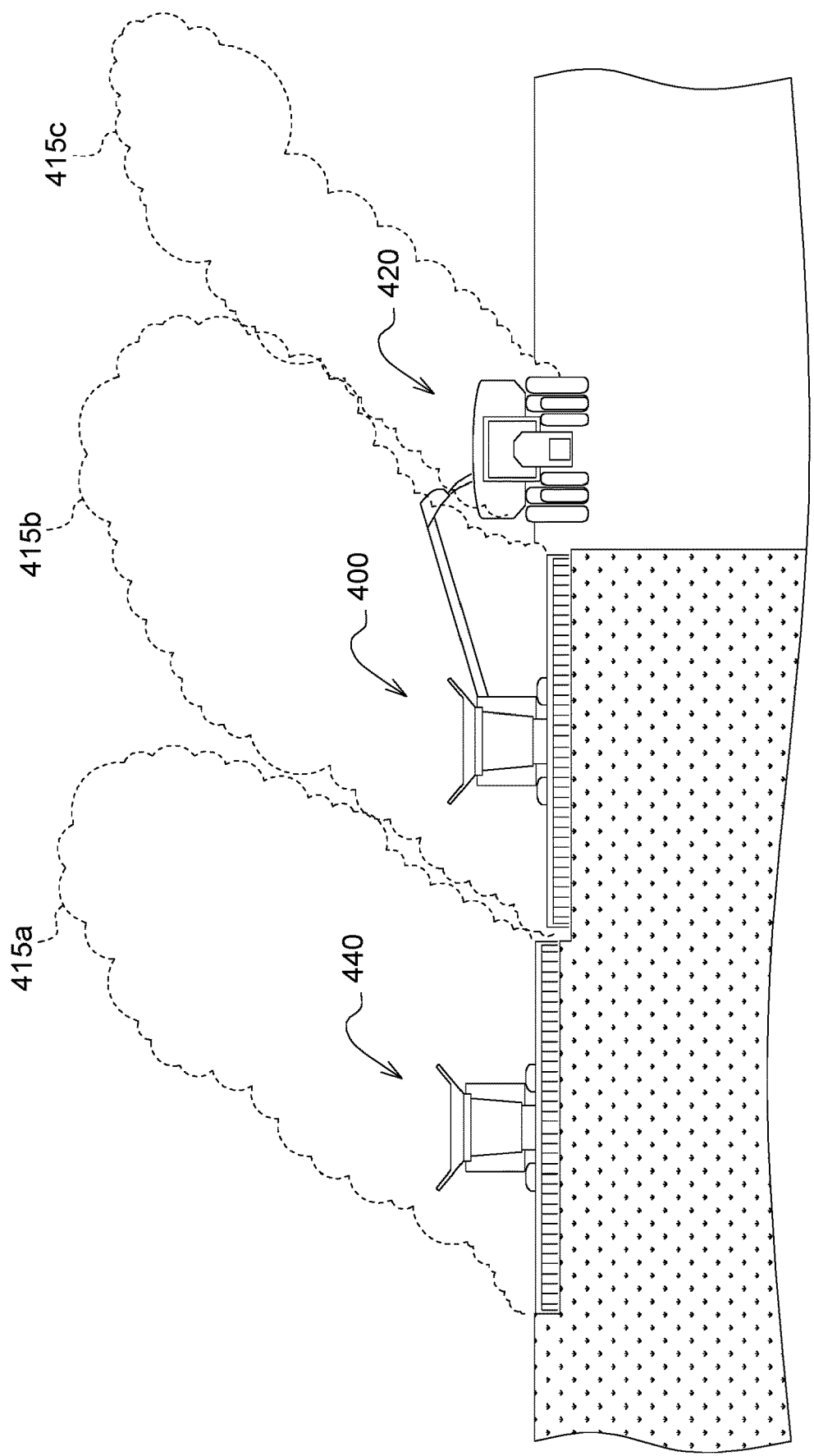
FIG. 3C is a front view of a work machine arrangement according to an embodiment.

Referring now to FIGS. 3A-3C, alternative work machine arrangements including two or more work machines are shown. In FIGS. 3A-3C, the alternative work machine arrangements include leader-follower arrangements comprising an agricultural harvester as the leader work machine, and a grain cart or a second harvester as the follower work machine. In the various embodiments, the vehicle sensors 120 and the obscurant mitigation system 150 can be arranged on either of the leader or follower work machines. For example, the vehicle sensors 120 can be mounted to an upper or lower frame of either of work machines, however, upper mounting can be particularly advantageous to reduce dust accumulation and/or prevent build-up of obscurants such as mud on the vehicle sensors 120. Similar to the embodiment discussed with reference to FIG. 1, the obscurant mitigation system 150 operates to mitigate airborne obscurants that impede and/or degrade the performance of the vehicle sensors 120.

As shown in FIG. 3A, environmental conditions such as wind conditions can impact the generation of obscurants and visibility of the vehicle sensors 120. The obscurant plume 215 is shown as being blown from right to left of the agricultural harvester 200 and the grain cart 220 based on a direction of wind travel as indicated by the arrow 202. In this exemplary embodiment, the forward sensing of the vehicle sensors 120 arranged on the grain cart 220 (i.e., follower work machine) may be impeded, for example, depending on the forward and back components of the wind.

Referring now to FIG. 3B, a similar leader-follower arrangement as that of FIG. 3A is shown. In FIG. 3B, the direction of wind travel causes the obscurants to be blown away from the agricultural harvester 300 and in an opposite direction as that of FIG. 3A. For example, a first obscurant plume 315a is generated at a rear of the agricultural harvester 300, and a second obscurant plume 315b is generated as grain is transferred into the follower work machine (i.e., grain cart 320). As shown, based on the location of the first and second obscurant plumes 315a, 315b, the forward perception of vehicle sensors 120 arranged on each of the work machines is unobstructed. Similarly, in FIG. 3C, the positioning of the work machines 400, 420 and 430 and the location of each of the obscurant plumes 415a, 415b, 415c is such that there is no obstruction of the forward perception of the vehicle sensors 120 arranged on each of the work machines 400, 420 and 430.

In either of the multi-work machine arrangements of FIGS. 3A-3C, it should be noted that it is possible to predict where obscurants may occur and to mitigate the obscurants through an in-field network as will be discussed in further detail with reference to FIGS. 9A and 9B. For example, in some embodiments, the work machines can communicate information such as current location, heading, speed, operation, operation details, wind conditions, expected path, and other critical data.

Figure 4:
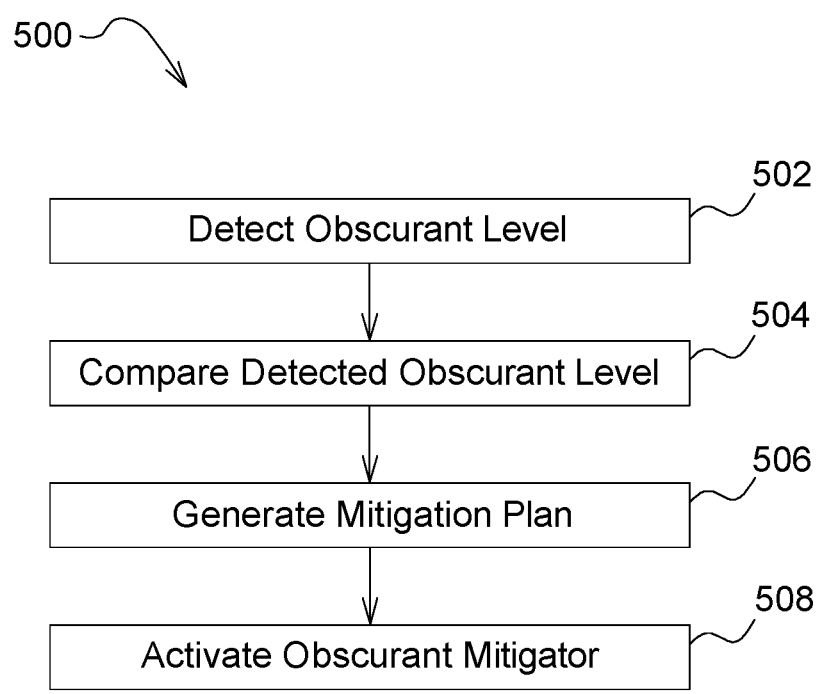
FIG. 4 is a flow diagram of a first method for detecting and mitigating obscurants.

Referring to FIG. 4, a flow diagram of a method 500 (i.e., a first method) for obscurant mitigation utilizing the obscurant mitigation system 150 in a single vehicle system (FIG. 1) is shown. At 502, an obscurant level is detected by the obscurant assessor 152 based on a characterization of the obscurant (obscurant plume). The obscurant assessor 152 can employ in situ measurement, modeling, physics-based equations, machine learning, case-based reasoning, or any other suitable technique or combinations of techniques to assess current and future obscurant levels and locations. For example, in some embodiments, the obscurant mitigation system 150 can further comprise a location-determining receiver (not shown) that allows for locations of the obscurant plumes to be georeferenced relative to the agricultural harvester 100 or other suitable frames of reference.

Next at 504, the obscurant assessor 152 transmits the measured obscurant level (e.g., visibility distance) to the controller 156 for processing. The controller 156 compares the obscurant level with a threshold value, which can be determined in real-time or retrieved from a stored database, to determine if the threshold value has been or will be exceeded. In some embodiments, the threshold value can be related to the needs of at least one of the vehicle sensors 120 based upon a desired mitigation output. For example, the threshold value (obscurant level) can be selected such that sensing functions are carried out for a certain distance from the vehicle sensors 120.

At 506, if the obscurant level exceeds the threshold value, the controller 156 generates a mitigation plan to reduce the obscurant level below the threshold value. For example, based upon the generated/determined mitigation plan, the controller 156 activates one or more components of the obscurant mitigator 154 to perform operations of the obscurant mitigation plan. In some embodiments, the one or more components can be common with core systems of the agricultural harvester 100, while in other embodiments, the components can be dedicated to obscurant mitigation.

In some embodiments, the obscurant mitigator 154 can be configured to perform positioning tasks such as spout positioning based on the determined mitigation plan. For example, as previously discussed with reference to FIG. 3B, the obscurant plume 315b can be generated by obscurant (e.g., dust) raised during transfer of material from the agricultural harvester 300 to the grain cart 320 through the spout 316. In such an embodiment, the obscurant mitigator 154, which can include a spout positioner, may operate to keep the spout 316 close to the crop material positioned inside the grain cart 320.

In other example embodiments, the obscurant mitigator 154 can reduce obscurant levels through path planning. For example, the obscurant mitigator 154 can comprise a path planner that facilitates the path of the agricultural harvester 300 specific to a standing crop. In such an embodiment, the standing crops can be used as a windbreak for tire and surface interaction, which in turn, reduces obscurant levels.

In still other embodiments, the controller 156 may command the obscurant mitigator 154 (e.g., a work machine speed controller) to reduce work machine speed in impaired worksite areas if a visibility distance is limited by obscurant (e.g., dust) blown from a non-irrigated area adjacent to a worksite, for example. Although such an embodiment does not operate to reduce the generated obscurants, mitigation can include reducing a visibility requirement of the agricultural harvester 100 when it is operating at lower speeds. If the visibility is impaired by obscurant generated by work machine tires or an attachment to the work machine such as a harvest head, blade, shank, etc., the amount of obscurant generated at the source may be reduced by decreasing work machine speed. In some embodiments, the obscurant assessor 152 can be used to estimate the obscurant level for a proposed work machine speed for comparison to the threshold value. In other embodiments, the obscurant assessor 152 can be configured to determine a maximum work machine speed based on the threshold value. For example, as described in commonly owned U.S. Pat. No. 9,043,129, the entirety of which is incorporated by reference herein, in some embodiments, the path plan can include a maximum work machine speed for segments of the path.

Referring to FIGS. 5A and 5B, an exemplary embodiment illustrating obscurant mitigation via path planning is shown. In FIGS. 5A and 5B, work machines 533 and 543 can be arranged to follow work machine paths 535 and 545. As the work machines 533 and 543 travel to worksites 531 and 541, obscurant plumes 537 and 547 are generated. In FIG. 5, obscurant plume 537 is blown towards the work machine 533 based on the direction of wind travel as indicated by the arrow 532 and impacts visibility vehicle sensors 539. In FIG. 5B, the work machine path 545 is orthogonal to a direction of the wind as indicated by the arrow 542, which, in turn, causes obscurant plume 547 to blow away from the work machine 543 and not obstruct the visibility of the vehicle sensors 549. As illustrated in FIG. 5B, obscurant mitigation utilizing path planning can be advantageous in facilitating removal of obscurants from the critical field of view of a work machine.

Figure 6:
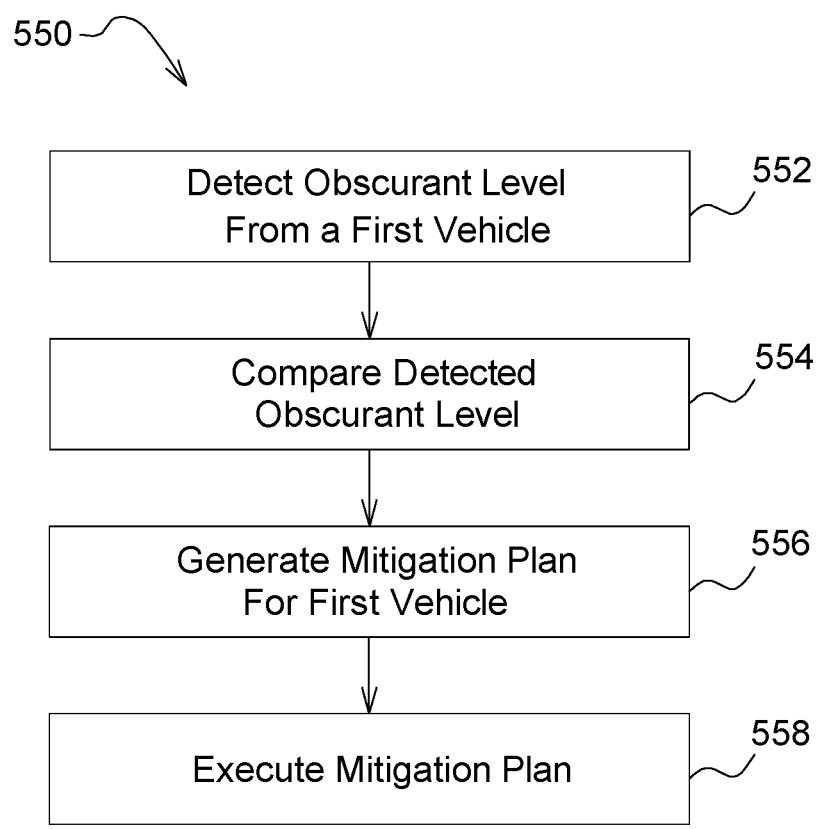
FIG. 6 is a flow diagram of a second method for detecting and mitigating obscurants.

Referring to FIG. 6, a flow diagram of a method 550 (i.e., a second method) for obscurant mitigation utilizing the obscurant mitigation system 150 in a multi-work machine arrangement is shown. At 552, the obscurant assessor 152 detects an obscurant level from a first work machine (e.g., work machine 603 or 703a) operating at a worksite (e.g., worksites 601 or 701). Next at 554, the obscurant assessor 152 transmits the measured obscurant level to the controller 156 for processing to determine if the obscurant level from first work machine exceeds the threshold value of a work machine sensor arranged on a second work machine (e.g., work machine 613 or 713b). At 556, if the obscurant level exceeds the threshold value, the controller 156 generates a mitigation plan to reduce the obscurant level generated at the first work machine below the threshold. To execute the obscurant mitigation plan, the controller 156 controls operations of the obscurant mitigator 154 for each of the first work machine and the second work machine.

In some embodiments, the methods 500 and 550 can be executed before work begins at the worksite or, in other embodiments, the methods can be executed while the work machine(s) are located at the worksites. This, in turn, allows for current environmental and obscurant data to be used in optimizing obscurant mitigation as will be discussed in further detail with reference to FIG. 10.

In FIGS. 7-9B, additional examples of multi-work machine use cases are shown. In the example embodiments, work machine data and obscurant data such as current heading, current planned path, obscurant optical density, plume direction from work machine, plume extent from work machine, and others will be used to generate a variety of obscurant mitigation plans. Additionally, data may be received at a first work machine from a second work machine over intermachine communication links. For example, in some embodiments, work machines on the worksite can cooperate as peers and self-organize. In other examples, one work machine may be designated as the leader. In such an arrangement, the leader work machine collects data from the follower work machines on the worksite and acts as a mission coordinator. In other embodiments, a remote processor (not shown) can be configured to collect data and coordinate operations of the work machines. For example, the work machines could take this information into account as autonomous agents, or the information from all the work machines could be aggregated into a "mission coordinator". The mission coordinator can continuously evaluate the information to determine each work machine's speed and future path segments to avoid potential obscurants generated by other work machines. For example, the mission coordinator may command the work machines to drive in a formation that reduces the impact of obscurants based on prevailing winds.

Figure 7:
FIG. 7 is an illustration of a work machine arrangement employing the second method according to an embodiment.

Referring now to FIGS. 7-9B, multi-work machine embodiments employing the method 550 are shown. In FIG. 7, a worksite 601, which is divided into two subzones 601a and 601b by dividing line 620, is shown. In the example illustration, wind 602 is blowing from left to right as indicated by the arrow 602. In some embodiments, the selected mitigation plan can include controlling, by the controller 156, at least one of a first work machine 603 or a second work machine 613 relative to the dividing line 620. For example, by choosing the dividing line 620 relative to wind 602, the first work machine 603 and the second work machine 613 can operate independently in each of the subzones 601a and 601b. This, in turn, allows for the obscurant plumes 607 and 617 generated by the first and second work machines 603, 613 to remain separated by the dividing line 620 as the work machines travel across the worksite 601, and prevents interference with the functionality of vehicle sensors (e.g., vehicle sensors 120) arranged on either of the work machines.

In other embodiments, the dividing line 620 can be implemented as a minimum separation distance between the first and second work machines 603, 613 relative to the direction of wind 602, which is determined by the controller 156.

Figure 8:
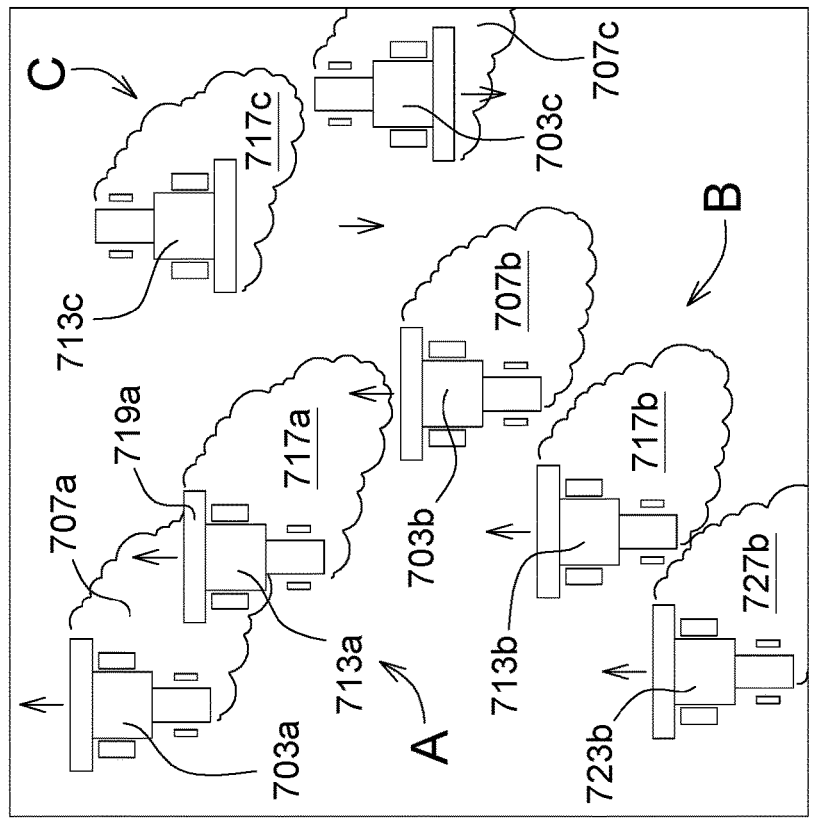
FIG. 8 is an illustration of a work machine arrangement employing the second method according to an embodiment.

In FIG. 8, a multi-vehicle arrangement is shown, which includes at least three sets of work machines operating in a wingman formation across a worksite 701 with wind blowing in a direction indicated by the arrow 702. A first set of work machines 703a, 713a can be arranged to form a first formation A. In the exemplary embodiment, the first formation A illustrates an undesirable mitigation arrangement of the first set of work machines 703a, 713a. For example, the work machines 703a, 713a are arranged such that an obscurant plume 707a generated by the work machine 703a interferes with an environmental sensor 719a of the work machine 713a. To mitigate such interference, the controller 156 can generate a mitigation plan including an operational rule or a path planning rule that causes the obscurant mitigator 154 to arrange a first work machine downwind of one or more second work machines. For example, the controller 156 can compute a minimum following distance as a function of wind direction and wind speed relative to a travel direction and speed of the work machines 703a, 713a, that allows for the work machines to be arranged relative to another in formations such as second formation B and third formation C. The second formation B can comprise three work machines 703b, 713b, and 723b having obscurant plumes 707b, 717b, and 727b, each arranged in offset relation relative to one another. Similarly, the third formation C can comprise at least two work machines 703c and 713c with obscurant plumes 707c and 717c arranged in offset relation.

Figure 9A:
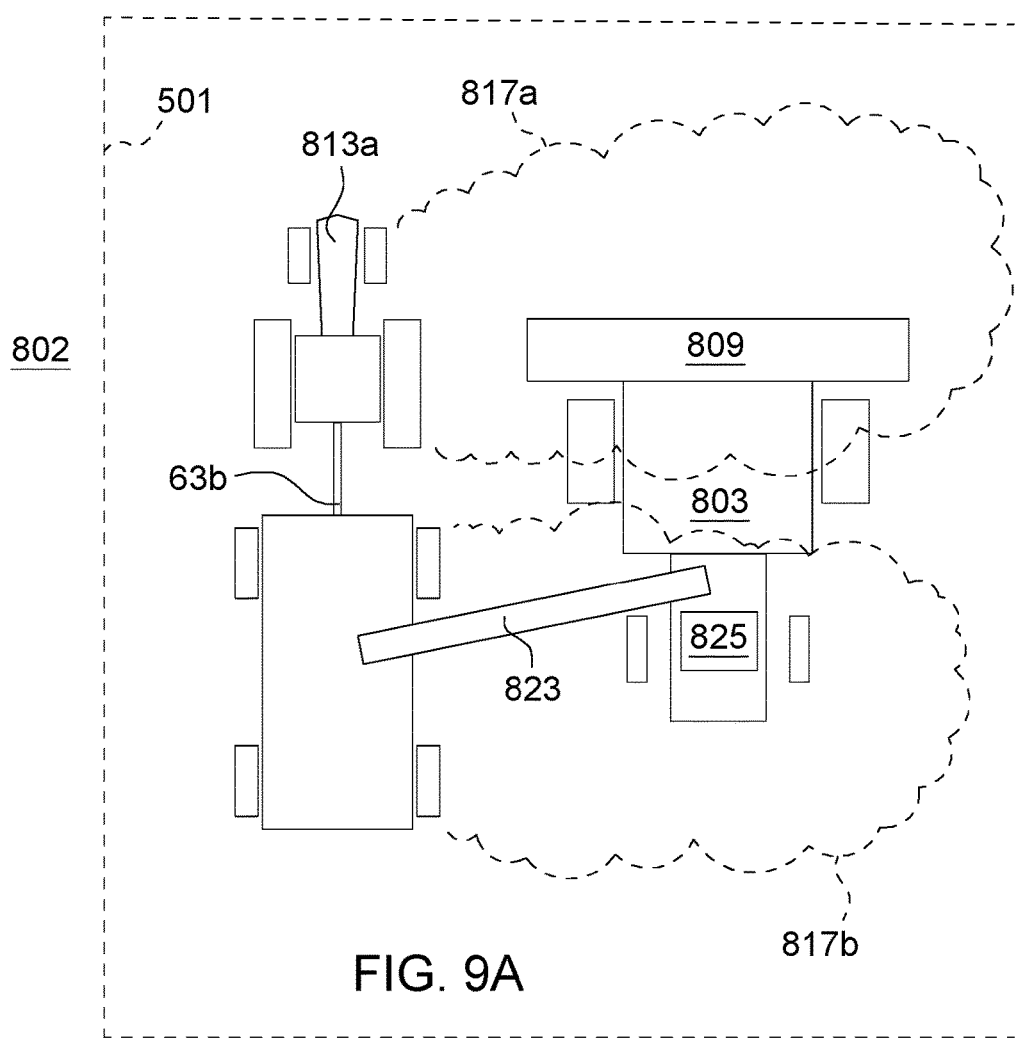
FIG. 9A is an illustration of a work machine arrangement employing the second method according to an embodiment.

In FIG. 9A, another embodiment of a multi-vehicle arrangement is shown. As previously discussed with reference to FIGS. 3A-3C, the multi-work machine arrangement can include a leader work machine 803 (e.g., an agricultural harvester) and at least two follower work machines 813a, 813b (e.g., a tractor and a grain cart). Each of the work machines 803, 813a, and 813b can travel across a worksite 801. In some embodiments, the leader work machine 803 can comprise an environmental sensor 809. A visibility or functionality of the environmental sensor 809 may be impaired by an obscurant plume 817a generated by the follower work machine 813b based on a direction of wind 802 and a relative arrangement of the environmental sensor 809 on the leader work machine 803.

In the example arrangement, the obscurant mitigation system 150 can generate one or more mitigation plans to reduce obscurant levels of obscurant plume 817a. In one embodiment, the mitigation system 150 can generate a path plan that directs the leader work machine 803 to travel a path that enables wind 802 to blow obscurant plume 817a away from the environmental sensor 809, the path planner may become constrained as a clean grain tank 825 is filled. As discussed with reference to FIG. 4, in other embodiments, mitigation tasks such as work machine speed control or material application could be used alone or in combination with one another to mitigate obscurant levels. It should be noted, however, that the independent subzone technique (i.e., subzones 601a, 601b) discussed with reference to FIG. 7 could not be implemented to mitigate obscurants associated with obscurant plume 817a for grain transfer operations. For example, to transfer grain between the work machines via a spout 823, the leader work machine 803 and the follower work machines 813a, 813b must be maintained in close proximity to another and therefore could not be arranged at a following distance relative to one another.

Figure 9B:
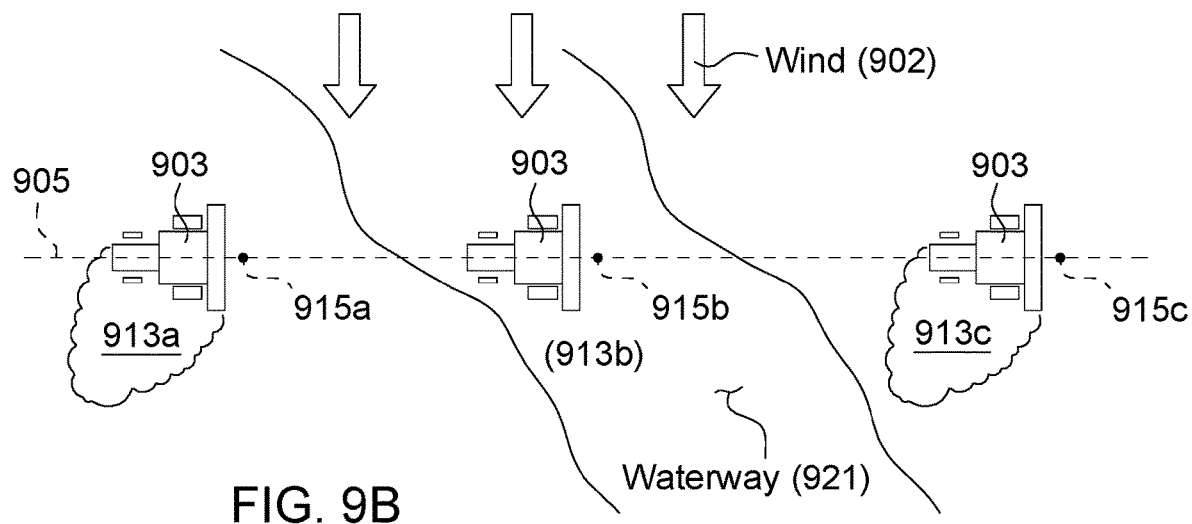
FIG. 9B is an illustration of a work machine arrangement employing the second method according to an embodiment.

Referring to FIG. 9B, an alternative multi-vehicle arrangement utilizing a path planning obscurant mitigation technique is shown. In the example embodiment of FIG. 9, obscurant plumes can be treated as dynamically sized keep-out zones, which are boundary zones or maps generated by the controller 156. For example, the controller 156 can optionally comprise a path planner module (not shown) that receives data from one or more of the obscurant sensors 151 and/or the obscurant assessor 152 to create path planning keep out zones based on characteristics of the obscurant plumes (e.g., obscurant plume 115, 215, or 315).

As shown in FIG. 9B, work machine 903 (e.g., an agricultural harvester) travels across a worksite 901 moving along a path segment 905 comprising points 905a, 905b, and 905c. At point 905a, the work machine 903 may generate an obscurant plume 913a which becomes a keep-out zone for the path planner module while the work machine 903 is at point 905a. The dynamically sized keep-out zone moves with the work machine 903. In other words, the path planner module generates a path plan to inhibit the work machine 903 from operating within at least a portion of the detected obscurant plume 913a (i.e., keep out zone). At point 905b on a waterway 921, an obscurant plume 913b is absent since there is no obscurant generated or chaff being spread. At point 905c, with different soil, crop, wind (i.e., wind 902), work machines, and other conditions, an obscurant plume and keep-out zone 913c having different size and shape characteristics can be identified.

Figure 10:
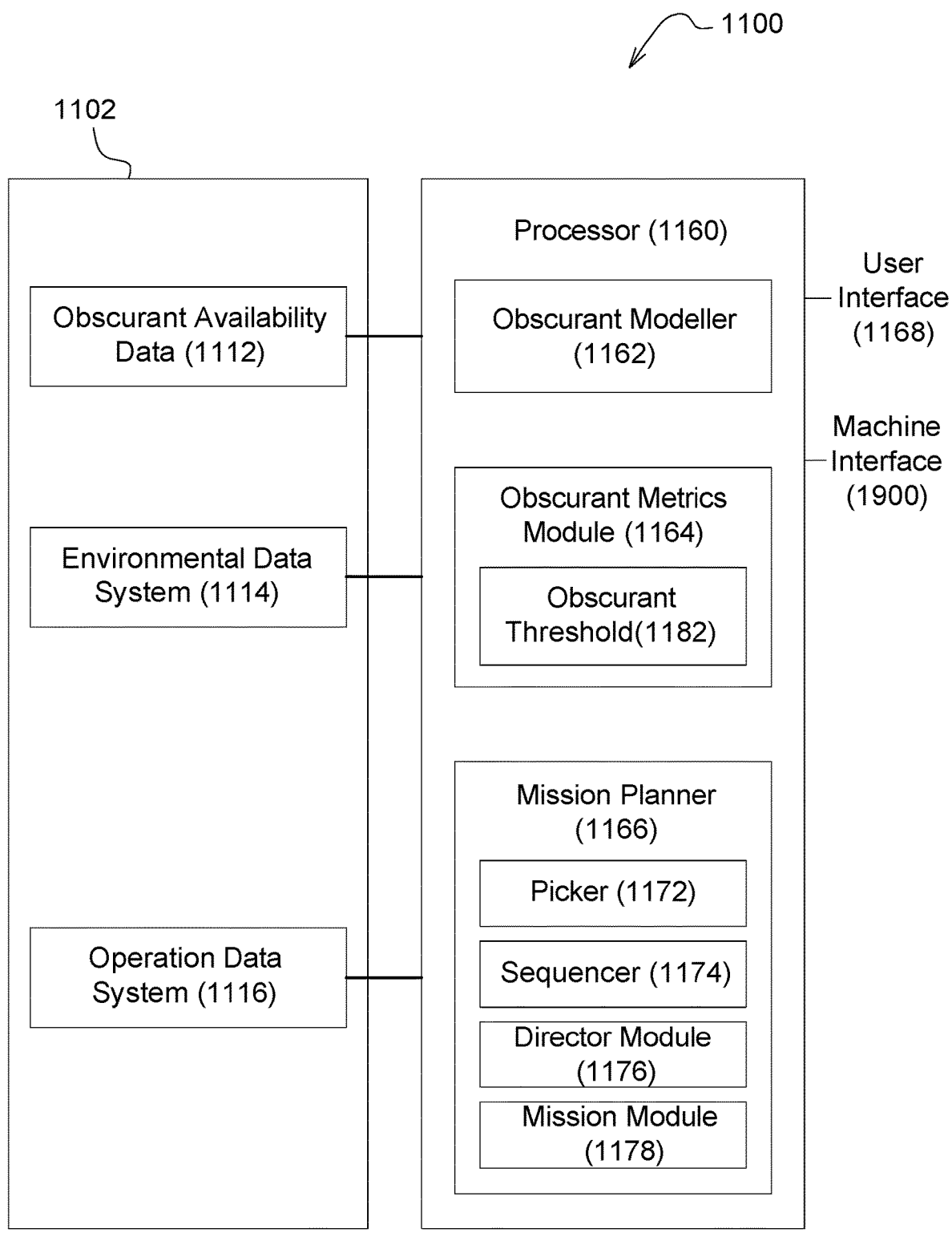
FIG. 10 is a block diagram of a mission planning system according to an embodiment.

Referring now to FIG. 10, in other embodiments, obscurant mitigation can be carried out by a mission planning system 1100. The mission planning system 1100 can prioritize worksites (e.g., worksites 2000, 3000, and 4000) based on predicted obscurant levels and mitigation opportunities for each of the worksites.

The mission planning system 1100 can comprise an electronic data processor 1160, which is substantially similar to the electronic data processor 160 discussed with reference to FIG. 1 and will not be discussed in detail, that receives sensor data and various information from an obscurant data system 1102. For example, the obscurant data system 1102 can comprise one or more data collection systems that collect and transmit obscurant related data to the electronic data processor 1160, which may be a single or multiprocessor (local, remote, or distributed). As shown in FIG. 10, in some embodiments, the obscurant data system 1102 can comprise an obscurant availability system 1112, an environmental data system 1114, and an operational data system 1116.

The obscurant availability system 1112 can collect obscurant data to determine current or forecast availability of obscurants at worksites 2000, 3000, 4000. In some embodiments, the obscurant availability system 1112 can comprise a plurality of obscurant sensors (e.g., obscurant sensors 151) arranged on one or more work machines (e.g., work machine 2020) at a single worksite or at multiple worksites. As previously discussed, the obscurant sensors can be configured to measure a variety of obscurant characteristics and attributes associated with a plume of obscurants (e.g., obscurant plume 115, 215, or 315). In some embodiments, the obscurant sensors can comprise one or more soil sensors that detect and monitor soil parameters such as soil type, soil moisture, soil cover (e.g., residue, standing crop), soil temperature, or other suitable soil parameters. Additionally, in other embodiments, the obscurant sensors can further comprise fog sensors, smoke sensors, or in situ or remote sensors such as weather radar that collect rain and/or snow data. Snow data, for example, can include historic or characteristic information about the condition of the snow (e.g., fluffy or non-thawed) and its ability to generate or suppress obscurants. The obscurant availability system 1112 may also collect work material related information to predict obscurant levels. For example, such information can be used to determine an amount of obscurants created or released by materials such as crop or piled sand based on interactions with the work vehicle 2020.

The environmental data system 1114 provides historic, current, or forecast environmental data related to the suppression, creation, transportation, or direction of obscurants. The environmental data system 1114 can comprise one or more environmental sensors that provide real-time monitoring of variables such as humidity, precipitation, wind, topography, temperature, particulate matter, or others which may impact the generation of obscurants.

For example, in some embodiments, the environmental sensors can monitor relatively high humidity conditions which may impact the generation of obscurants such as fog. In precipitous conditions such as in rain or snow, obscurants can be created or suppressed based on the type of obscurant. For example, obscurants such as dust may be suppressed for a period of time by rain or snow. Intense wind conditions can impact how obscurants such as soil, smoke, snow, and work material are transported or generated based on a direction of wind travel. Additionally, topography can shelter or amplify wind as well as impact soil moisture. Obscurant availability may also be impacted by temperature changes. For example, rising temperatures with a constant dewpoint can change the prevalence of fog. Snow which thaws and refreezes to form a crust is less likely to blow, as well as frozen soil. Airborne particulate matter and other data may be considered also.

In other embodiments, the environmental data system 1114 can retrieve data from an environmental database 1130 that stores current and historic weather information, or environmental features of the operating environment that may impact the work machine 2020. In other alternative embodiments, the environmental data system 1114 can receive local, regional, and national weather service updates from a remote processing center (not shown).

The operational data system 1116 can receive data related to the functions, activities, and components of the work machine 2020 that may have a direct or indirect impact on obscurants. For example, in some embodiments, the operational data system 1116 can receive inputs from one or more sensors such as vehicle sensors 120 previously discussed with reference to FIG. 1. The vehicle sensors 120 can output information (e.g., a visibility condition) about the sensor such as whether a view of the sensor is obstructed or if the sensor has reduced visibility based on obscurant generation. The operational data system 1116 may also receive inputs from a tire monitoring system (not shown). The data may include information such as a tire tread or inflation level, which may impact the generation of obscurants such as dust. The operational data system 1116 may also include information about the relative locations of vehicle components that could generate an obscurant and the vehicle sensors which could be impaired by the obscurant.

The operational data system 1116 may also monitor parameters of the work machine such as vehicle speed, material transfer rate, and material transfer to generate obscurant data. For example, activities such as movement of the work machine across the worksite or transfer of material into a grain tank can cause obscurants to become airborne. This obscurant data can, in turn, be correlated to one or more of the vehicle parameters to determine an amount of airborne obscurant.

Referring now to FIG. 10, the electronic data processor 1160 can comprise a computer readable storage medium having executable instructions that are used to implement one or more software modules to carry out functions of the mission planning system 1100. In some embodiments, the one or more software modules can comprise an obscurant modeler 1162, an obscurant metrics module 1164, and a mission planner 1166.

In some embodiments, the obscurant modeler 1162 can receive data from each of the data systems (i.e., obscurant availability system 1112, environmental data system 1114, operational data system 1116) of the obscurant data system 1102 to generate models of obscurant plumes. The obscurant metrics module 1164 can generate a plurality of obscurant metrics. The obscurant metrics can include a computed value related to a quantity of obscurants. The obscurant metrics can also be generated based on worksite data. For example, in some embodiments, the obscurant metrics module 1164 can receive worksite data from the obscurant data system 1102. Such information can include obscurant data collected from a single worksite at various times, a number of different worksites at a specific time, or several different worksites at various times. In some embodiments, the obscurant metrics module 1164 can comprise an obscurant threshold database 1182 that stores predetermined threshold values, which may be in the form of a look-up table. Without limitation, obscurant metrics may be related to an attenuation of a signal, a blurring of an image, a partial blockage of a signal or image, a distortion of a signal or image, a distance a sensor is able to sense relative to a work machine, or a time of image acquisition.

The mission planner 1166 receives obscurant metrics generated by the obscurant modeler 1162 to coordinate missions of the work machine 2020. The mission planner 1166 can sequence operations of the one or more work machines based on the obscurant metrics. For example, the mission planner 1166 can determine the best time to perform missions at a single worksite, the best worksite for carrying out a mission at a given time, and the best worksite sequence over time as will be discussed with reference to FIGS. 11-13.

Figure 13:
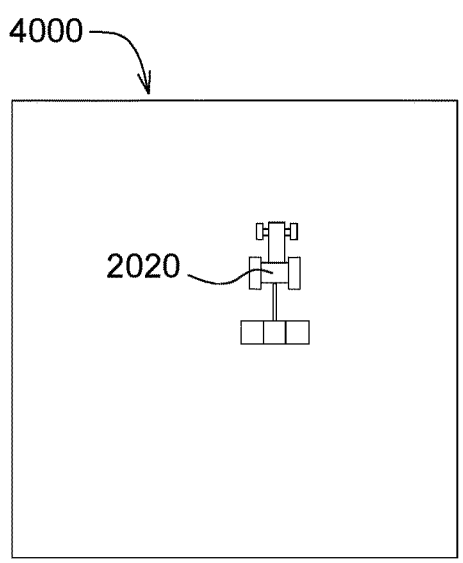
FIG. 13 is an illustration of a work machine employing the mission planning system of FIG. 10 according to an embodiment.

The mission planner 1166 can comprise program instructions comprising a picker 1172, a sequencer 1174, a director module 1176, and a mission module 1178. The picker 1172 picks the best time for a mission at a worksite (e.g., worksite 2000) and the best worksite for carrying out a mission at a given time. The sequencer 1174 communicates with the mission module 1178 to sequence missions at two or more worksites at varying times (FIG. 13). The director module 1176 can comprise control instructions for directing the work machine 2020 on the worksite based on information received from the picker 1172 and the sequencer 1174. For example, the director module 1176 can direct the operations of work machine 2020 to at least one of worksites 2000, 3000, or 4000. The mission module 1178 can use information such as machine identification (each machine can be assigned an ID or specific task), worksite locations, mission start and end times, work machine path plan(s), work machine speed at one or more locations on a path, work machine settings such as material transfer rate or material drop distance to generate a selection of missions to be carried out by the work machine 2020.

In various embodiments, the program instructions may be modified or dynamically recalculated on the worksite while the mission is being carried out by a work machine based on new local or remotely sensed data. Additionally, the program instructions may also be modified via the user interface 1168. For example, a user may input new or updated information, commands, or preferences into the user interface 1168, which are received and processed by the electronic data processor 1160. The user interface 1168 may be local or remote and, similar to user interface 168, may also employ visual, audio, speech, haptic, or any other suitable communication means.

Figure 11:
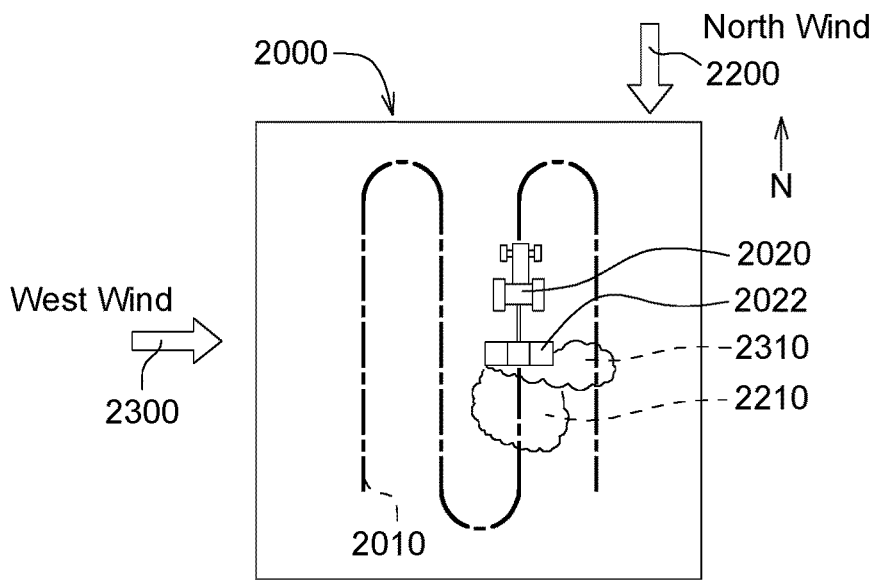
FIG. 11 is an illustration of a work machine employing the mission planning system of FIG. 10 according to an embodiment.

Referring now to FIG. 11, an exemplary embodiment of a work machine 2020 employing the mission planning system 1100 is shown. In FIG. 11 a worksite 2000 where early season tillage is to be done along a path 2010 by the work machine 2020 is shown. In operation, the mission planning system 1100 can determine the best time tillage operations should be performed at the worksite 2000 based on obscurant data.

As previously discussed, the electronic data processor 1160 can receive obscurant related information about the worksite 2000 from the obscurant data system 1102. For example, the operational data system 1112 can receive operation data about the work machine 2020 via an optical sensor 2022. As shown in FIG. 11, the optical sensor 2022 can be arranged rearward of the work machine 2020 to monitor tillage quality (obscurant plumes 2210 and 2310). The path 2010 can be formed in a north-south direction in support of planting and later worksite operations.

Next, the environmental data system 1114 can receive environmental data such as topographical, wind, and/or precipitation data about the worksite 2000. For example, in some embodiments, the environmental data system 1114 may receive topographical data indicating that the worksite 2000 has a generally flat topography which is incapable of blocking, channeling, or enhancing winds such as north wind 2200 and west wind 2300. Additionally, system 1114 may receive information about wind conditions of the worksite 2000. For example, such information can include a forecast predicting that a 35-mph wind such as north wind 2200 will occur at 9 am and switch to a 35-mph west wind 2202 by 3 pm. Other environmental data may include a forecast indicating that the worksite 2000 has insufficient precipitation for dust suppression to allow for field work to be completed.

The obscurant availability system 1112 can receive obscurant data about the worksite 2000. For example, in some embodiments, the obscurant availability system 1112 can receive satellite image data and university extension ground data which indicate that the worksite 2000 has dry soil surface conditions. Other data may include information about the soil indicating, e.g., that the worksite 2000 has a soil type that is high in silt.

Based on the data received from the obscurant data system 1102, the electronic data processor 1160 can determine an optimal time for carrying out operations (e.g., tillage operations) at the worksite 2000 and directs the work machine to the worksite 2000 accordingly.

As shown in FIG. 11, the obscurant modeler 1162 can generate models of a north wind dust plume 2210 and a west wind dust plume 2310 as the work machine 2020 follows the path 2010. For each of the two plume scenarios, obscurant metrics can be generated by the obscurant metrics module 1164. For example, using the below cost function, it can be determined that a north wind 2200 will cause the optical sensor 2022 to be 90% obscured when work machine 2020 is traveling north and 10% obscured when the work machine 2020 is traveling south. For example, based on the north and south travel of the work machine 2020, which is evenly split 50-50, the obscurant modeler 1162 can determine an obscurant metric based on the below cost function:

$$(90\% \times 50\%) + (10\% \times 50\%) \times 100 = 50.$$

Similarly, the electronic data processor 1160 can determine that the west wind 2300 will cause the optical sensor 2022 to be obscured 15% when traveling in both the north and south directions. The obscurant modeler 1162 can determine an obscurant metric based on the below cost function:

$$(15\% \times 100\%) \times 100 = 15.$$

In this example, the electronic data processor 1160 can determine that the work machine 2020 should proceed with a mission at worksite 2000 if the computed obscurant metric falls below a predetermined threshold value of 20, which can be retrieved from the obscurant threshold database 1182. The electronic data processor 1160 can display the results on the user interface 1168. Additionally, the electronic data processor 1160 can execute the tillage mission via machine interface 1900 to direct the work machine 2020 to arrive at worksite 2000 at 3 pm. In some embodiments, directions may comprise delivering work instructions to a human operator via the user interface 1168. In other embodiments, the electronic data processor 1160 may autonomously operate the work machine 2020 to the work site 2000. The electronic data processor 1160 may also communicate the directions to a vehicle controller, which, in turn, can halt tillage operations of the work machine 2020 at worksite 2000 until the west wind or some other condition is met.

Figure 12:
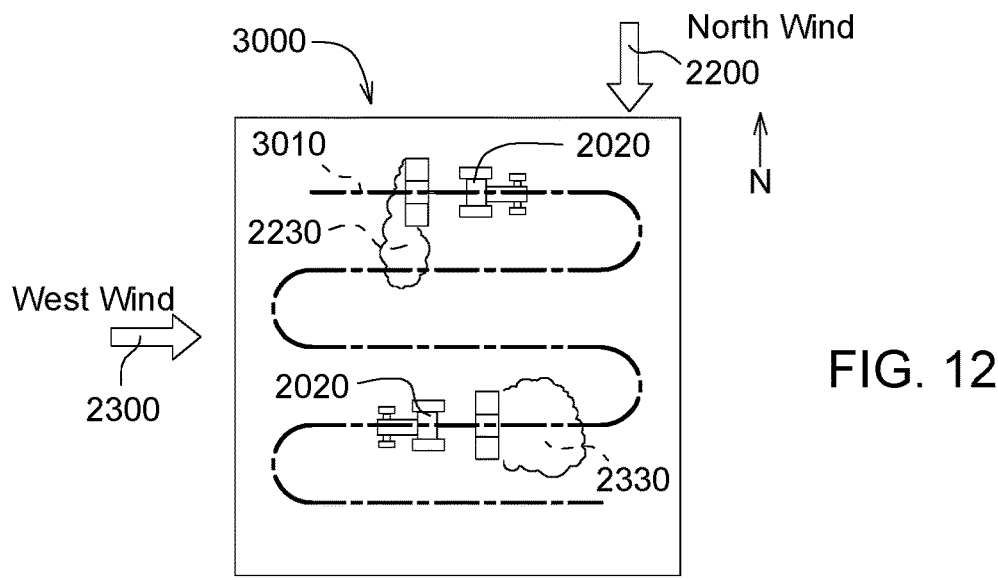
FIG. 12 is an illustration of a work machine employing the mission planning system of FIG. 10 according to an embodiment.

In other embodiments, referring now to FIG. 12, the mission planning system 1100 can determine that operations of the work machine 2020 should be carried out at a worksite such as worksite 3000. It should be noted that worksite 3000 is substantially similar to worksite 2000 except that worksite 3000 includes a path 3010 that runs east to west rather than north to south. Based on data received from the obscurant data system 1102, the electronic data processor data 1168 can direct the work machine 2020 to worksite 2000 or 3000 based on an associated obscurant metric. For example, the electronic data processor 1168 can determine which worksite (i.e., worksite 2000 or 3000) should be tilled at 9 am based on the obscurant metrics. The worksite 2000 may have an obscurant metric of 50 and worksite 3000 may have an obscurant metric of 13. Since worksite 3000 has a lower obscurant metric, the electronic data processor 1168 can determine that worksite 3000 is the best worksite for performing tilling operations at 9 am and direct the work machine 2020 to the worksite 3000.

Referring to FIG. 13, a worksite 4000 is shown. The worksite 4000 has distinct soil and topography features from those of worksite 2000 and 3000, which can lead to increased obscurant metrics. The worksite 4000 can include a variety of paths which can be taken by the work machine 2020.

In this example, data can be generated by the environmental data system 1114 forecasting a light overnight shower that will suppress and settle dust on each of the worksites 2000, 3000, and 4000, and a west wind (not shown) of 10 mph for day 2.

Based on obscurant data received from the obscurant data system 1102, the obscurant metrics module 1164 generates the following worksite obscurant metrics as shown in Table 1 below.

TABLE 1

| Work Site   | 2000 | 3000 | 4000 |
|-------------|------|------|------|
| Day 1: 9 AM | 50   | 15   | 60   |
| Day 1: 3 PM | 15   | 50   | 25   |
| Day 2: 9 AM | 5    | 10   | 18   |

It should be noted that a lower obscurant metric is indicative of better operating environments for each of the worksites 2000, 3000, 4000. As illustrated in the above table, the obscurant metrics for worksite 4000 are high on day 1 at 9 am but can be reduced on day 2 after rain and wind reductions. As such, the mission module 1178 sequences operations for worksites 2000 and 3000 on day 1, and to worksite 4000 on day 2 based on the lower obscurant metrics. The work machine 2020 is directed to worksite 3000 at 9 am on day 1; to worksite 2000 at 3 pm on day 1; and to worksite 4000 at 9 am on day 2 with a desirable north-south path plan. The preceding examples were without limitation and kept simple to aid explanation of the invention.

Without in any way limiting the scope, interpretation, or application of the claims appearing below, a technical effect of one or more of the example embodiments disclosed herein is a mission planning system and method.

While the above describes example embodiments of the present disclosure, these descriptions should not be viewed in a limiting sense. Rather, other variations and modifications may be made without departing from the scope and spirit of the present disclosure as defined in the appended claims. For example, in other embodiments, the obscurant mitigation system can further comprise feature tracking and visual odometry techniques that are used to determine the size, location, density of obscurants. Such techniques may be used to associate obscurants with tracked features such as where there is a reduction in the quality of tracked features in a certain image region, this data may be an indication of obscurants in that region. The density of the obscurant can be correlated to the reduction in quality of the feature. In other alternative embodiments, the relative location of those features can be measured, and the area of the affected region estimated if, e.g., the feature tracking is performed with a stereo camera. The feature tracking may also help to identify the motion vector of the obscurant.

What is claimed is:

1. A system for obscurant mitigation, the system comprising:
    an obscurant assessor, wherein the obscurant assessor is configured to characterize one or more attributes of a detected obscurant plume, which is airborne, and generate an obscurant model;
    an obscurant mitigator, wherein the obscurant mitigator is configured to perform one or more mitigation operations to mitigate detected obscurant plume to increase visibility of a vehicle sensor; and
    a controller communicatively coupled to each of the obscurant assessor and the obscurant mitigator, wherein the controller is configured to:
        receive an output signal from the vehicle sensor corresponding to a detected obscurant level and determine if the detected obscurant level exceeds a predetermined threshold;
        generate an obscurant mitigation plan if the detected obscurant level exceeds the predetermined threshold based on the obscurant model generated by the obscurant assessor, wherein generating an obscurant mitigation plan comprises modifying an operation of a ground engaging member coupled to a work vehicle; and
        control operations of the obscurant mitigator based on the obscurant mitigation plan to reduce the detected obscurant level to increase visibility of the vehicle sensor.

2. The system of claim 1, wherein the vehicle sensor is coupled to the work vehicle, and wherein the detected obscurant level corresponds to a quantity of obscurants located within an area surrounding the work vehicle.

3. The system of claim 1, wherein the obscurant assessor further comprises one or more obscurant sensors comprising one or more of the following: laser sensors, density sensors, cameras, thermal imaging sensors, or combinations thereof.

4. The system of claim 1, wherein characterizing one or more attributes of the detected obscurant comprises assessing current and future obscurant levels, and corresponding location data.

5. The system of claim 4, wherein the attributes comprises one or more of the following properties: particle density, particle size, particle size distribution, or combinations thereof.

6. The system of claim 1, wherein generating an obscurant mitigation plan comprises generating a path plan for the work vehicle to inhibit the work vehicle from operating within at least a portion of the detected obscurant plume to prevent an impairment of the visibility of the vehicle sensor.

7. The system of claim 1, wherein modifying the operation of the ground engaging member comprises adjusting a depth of the ground engaging member in the ground.

8. The system of claim 1, further comprising generating an alert for an operator display when the detected obscurant level is reduced below the predetermined threshold.

9. The system of claim 1, further comprising an agricultural work vehicle having the vehicle sensor capturing images in a field of view.

10. A system for obscurant mitigation arranged in a work vehicle, the system comprising:
    an obscurant assessor arranged on at least one of a first work vehicle and a second work vehicle, wherein the obscurant assessor is configured to characterize one or more attributes of a detected obscurant at least generated by the first work vehicle and generate an obscurant model;
    an obscurant mitigator, wherein the obscurant mitigator is configured to perform one or more mitigation operations to mitigate the detected obscurant, which is airborne; and
    a controller communicatively coupled to each of the obscurant assessor and the obscurant mitigator, wherein the controller is configured to:
        receive an output signal from a vehicle sensor corresponding to a detected obscurant level of the detected obscurant at least generated by the first work vehicle and determine if the detected obscurant level exceeds a predetermined threshold associated with the second work vehicle;
        generate an obscurant mitigation plan if the detected obscurant level exceeds the predetermined threshold based on the obscurant model generated by the obscurant assessor; and
        control operations of the obscurant mitigator to control each of the first work vehicle and the second work vehicle based on the obscurant mitigation plan to reduce the detected obscurant level to increase visibility of the vehicle sensor.

11. The system of claim 10, wherein the vehicle sensor is coupled to at least one of the first work vehicle or the second work vehicle, and wherein the detected obscurant level corresponds to a quantity of obscurants located within an area surrounding the first or second work vehicle.

12. The system of claim 10, wherein the obscurant mitigation plan includes controlling, by the controller, at least one of the first work vehicle and the second work vehicle relative to a dividing line such that a first obscurant plume generated by the first work vehicle and a second obscurant plume generated by the second work vehicle remain separated by the dividing line.

13. The system of claim 12, wherein the dividing line is chosen relative to wind.

14. The system of claim 13, wherein the dividing line is implemented as a minimum separation distance between the first work vehicle and the second work vehicle.

15. The system of claim 10, wherein the obscurant mitigation plan includes an operational rule or a path planning rule that causes the obscurant mitigator to arrange a first work vehicle downwind of the second work vehicle.

16. The system of claim 15, wherein the controller is configured to compute a minimum following distance between the first work vehicle and the second work vehicle as a function of wind direction and wind speed relative to a travel direction and speed of the first and second work vehicles.

17. The system of claim 10, wherein grains are transferred between the first and the second work vehicles during the operations of the obscurant mitigator.

18. A method for obscurant mitigation, the method comprising:
    detecting a level of obscurant, which is airborne, with an obscurant assessor;
    comparing, with a controller, the detected level of obscurant with a threshold value to determine if the detected level exceeds the threshold value;
    generating, with the controller, an obscurant mitigation plan if the detected level exceeds the threshold value, wherein generating an obscurant mitigation plan comprises modifying an operation of a ground engaging member coupled to a work vehicle; and
    controlling at least one obscurant mitigator based on the generated obscurant mitigation plan to mitigate a detected obscurant plume to increase performance of a vehicle sensors.

19. The method of claim 18, wherein detecting a level of obscurant further comprises characterizing one or more attributes to assess current and future obscurant levels, and corresponding location data.

20. The method of claim 18, wherein generating an obscurant mitigation plan comprises generating a path plan for the work vehicle to inhibit the work vehicle from operating within at least a portion of a detected obscurant plume to prevent an impairment of the visibility of the vehicle sensor.

21. The method of claim 18, wherein detecting a level of obscurant comprises detecting a level of obscurant associated with a first work vehicle.

22. The method of claim 21, wherein the detected level of obscurant associated with the first work vehicle is compared with a threshold value for a second work vehicle; and wherein an obscurant mitigation plan is generated to control each of the first work vehicle and the second work vehicle if the detected level of obscurant exceeds the threshold value.

* * * * *